United States Patent
Bovell et al.

(10) Patent No.: US 10,227,594 B2
(45) Date of Patent: Mar. 12, 2019

(54) ANTIPERSPIRANT COMPOSITION

(71) Applicant: Conopco, Inc., Englewood Cliffs, NJ (US)

(72) Inventors: Douglas Bovell, Bishopton (GB); Richard Livesey Evans, Liverpool (GB); Jennifer Robertson, Stirlingshire (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/556,462

(22) PCT Filed: Mar. 10, 2016

(86) PCT No.: PCT/EP2016/055157
§ 371 (c)(1),
(2) Date: Sep. 7, 2017

(87) PCT Pub. No.: WO2016/150723
PCT Pub. Date: Sep. 29, 2016

(65) Prior Publication Data
US 2018/0037894 A1    Feb. 8, 2018

(30) Foreign Application Priority Data

Mar. 20, 2015 (EP) .................... 15160174

(51) Int. Cl.
| | | |
|---|---|---|
| *C07H 21/02* | (2006.01) | |
| *C07H 21/04* | (2006.01) | |
| *C12N 15/113* | (2010.01) | |
| *A61K 8/60* | (2006.01) | |
| *A61Q 15/00* | (2006.01) | |

(52) U.S. Cl.
CPC .......... *C12N 15/1138* (2013.01); *A61K 8/606* (2013.01); *A61Q 15/00* (2013.01); *C12N 2310/14* (2013.01)

(58) Field of Classification Search
CPC ............................ A61K 31/713; C12N 15/113
See application file for complete search history.

(56) References Cited

U.S. PATENT DOCUMENTS

| | | |
|---|---|---|
| 7,087,743 B2 | 8/2006 | Kurfurst |
| 7,504,385 B2 | 3/2009 | Binetti |
| 8,618,160 B2 | 12/2013 | Johnston et al. |
| 2005/0222071 A1 | 10/2005 | Duranton |
| 2005/0261222 A1 | 11/2005 | Wolber |
| 2006/0211620 A1 | 9/2006 | Schnorr |
| 2006/0272050 A1 | 11/2006 | Segura |
| 2007/0134188 A1 | 6/2007 | Collin-Djangone |
| 2008/0207737 A1 | 8/2008 | Zinger |
| 2010/0209934 A1 | 8/2010 | Oh |
| 2010/0227803 A1 | 9/2010 | Spodsberg |
| 2011/0054005 A1 | 3/2011 | Naito et al. |
| 2012/0190627 A1 | 7/2012 | Delattre |

FOREIGN PATENT DOCUMENTS

| | | | |
|---|---|---|---|
| DE | 102005001784 | 10/2006 | |
| EP | 1752536 | 2/2007 | |
| EP | 2213738 | 8/2010 | |
| EP | 2 865 758 A1 * | 10/2013 | ........... C12N 15/113 |
| WO | WO0112806 | 2/2001 | |
| WO | WO0211690 | 2/2002 | |
| WO | WO2009001359 | 12/2008 | |
| WO | WO2010080452 | 7/2010 | |
| WO | WO2013120726 | 8/2013 | |
| WO | WO14027050 | 2/2014 | |
| WO | WO2014107124 | 7/2014 | |

OTHER PUBLICATIONS

Min Seuk Kim et al., Native Store-operated Ca2+ Influx Requires the Channel Function of Orail and TRPC1, The Journal of Biological Chemistry, Apr. 10, 2009, XP055211577, vol. 284 No. 15, pp. 9733-9741.
Potier et al., Evidence for STIM1- and Orai1-dependent store-operated calcium influx through ICRAC in vascualr smooth muscle cells: role in proliferation and migration, The FASEB Journal, 2009, XP002744090 and; XP055211561, vol. 23, No. 8, pp. 2425-2437 and pp. 1-9.
Saliba et al., Emergence of Orai3 activity during cardiac hypertrophy, Cardiovascular Research, 2015, XP055211576, vol. 105, No. 3, pp. 248-259.
Search Report and Written Opinion in EP15160174, dated Oct. 21, 2015.
Search Report and Written Opinion in PCTEP2016055157, dated Apr. 26, 2016.
Search Report in EP15160174, dated Sep. 7, 2015.
Stanisz et al., Inverse regulation of melanoma growth and migration by Orai1/STIM2-dependent calcium entry, Pigment Cell & Melanoma Research, 2013, XP002744092, pp. 1-38.
Stanisz et al., Inverse regulation of melanoma growth and migration by Orai1/STIM2-dependent calcium entry, Pigment Cell & Melanoma Research, 2014, XP002744091, vol. 27 No. 3, pp. 442-453.
Suganuma et al., STIM1 Regulates Platelet-Derived Growth Factor-Induced Migration and Ca2+ Influx in Human Airway Smooth Muscle Cells, PLOS ONE, 2012, XP055211570, vol. 7, No. 9, pp. 19.

* cited by examiner

*Primary Examiner* — Amy H Bowman
(74) *Attorney, Agent, or Firm* — Greenberg Traurig, LLP

(57) ABSTRACT

A method of reducing perspiration comprising the topical application of a composition comprising an siRNA that is capable of reducing levels of a specified protein or its mRNA or the function or formation of calcium channel associated therewith; wherein the specified protein is Orai1, Stim1, Orai3, TRPC1 or Stim2.

Figure 1:
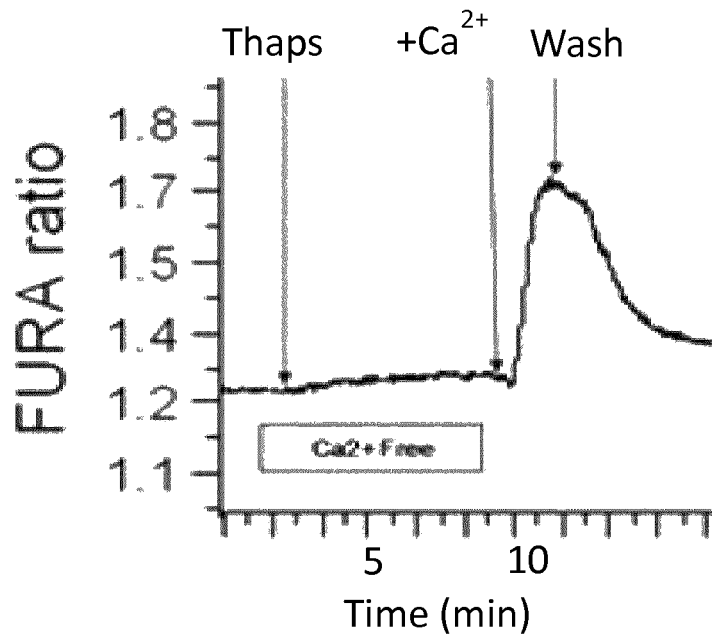

7 Claims, 1 Drawing Sheet
Specification includes a Sequence Listing.

SEQUENCE LISTING

<160> NUMBER OF SEQ ID NOS: 5

<210> SEQ ID NO 1
<211> LENGTH: 20
<212> TYPE: RNA
<213> ORGANISM: Artificial Sequence
<220> FEATURE:
<223> OTHER INFORMATION: siRNA oligonucleotide sequence

```
<400> SEQUENCE: 1
ccuugaccga guugagauug                                           20

<210> SEQ ID NO 2
<211> LENGTH: 20
<212> TYPE: RNA
<213> ORGANISM: Artificial Sequence
<220> FEATURE:
<223> OTHER INFORMATION: siRNA oligonucleotide sequence

<400> SEQUENCE: 2
uggaguaacg guucuggaua                                           20

<210> SEQ ID NO 3
<211> LENGTH: 20
<212> TYPE: RNA
<213> ORGANISM: Artificial Sequence
<220> FEATURE:
<223> OTHER INFORMATION: siRNA oligonucleotide sequence

<400> SEQUENCE: 3
gauucaguuc cucuaguucc                                           20

<210> SEQ ID NO 4
<211> LENGTH: 20
<212> TYPE: RNA
<213> ORGANISM: Artificial Sequence
<220> FEATURE:
<223> OTHER INFORMATION: siRNA oligonucleotide sequence

<400> SEQUENCE: 4
uguugugagc aaccacuuug                                           20

<210> SEQ ID NO 5
<211> LENGTH: 20
<212> TYPE: RNA
<213> ORGANISM: Artificial Sequence
<220> FEATURE:
<223> OTHER INFORMATION: siRNA oligonucleotide sequence

<400> SEQUENCE: 5
uauuguagua uugcacuucu                                           20
```

ANTIPERSPIRANT COMPOSITION

The present invention relates to an antiperspirant composition and a method of reducing perspiration from the human skin.

Many antiperspirancy actives, compositions and methods have been reported. Typical antiperspirant actives are synthetic astringent salts based on aluminum and/or zirconium and these operate by blocking or partially blocking the sweat ducts on the surface of the human body and thereby reducing perspiration.

Other antiperspirancy methods have been devised that involve reducing the amount of sweat produced at its source, i.e. the secretory coils of the sweat glands, in particular, the eccrine glands. Some of these have been claimed as treatments for hyperhidrosis.

WO 02/011690 (Unilever) discloses an antiperspirancy method whereby calcium channels with the secretory coil cells of the eccrine glands are blocked, thereby controlling sweat production at its source.

U.S. Pat. No. 8,618,160 B2 (Rose U) discloses wipes containing glycopyrrolate, a muscarinic anticholinergic, as a treatment for hyperhidrosis.

Certain anticholinergic drugs have also been used to treat hyperhidrosis, with varying degrees of success. These drugs include Ditropan® (oxybutynin), Probanthine® (propantheline bromide) and Cogentin® (benzotropine).

US 2008/0207737 (Zinger) discloses a topical composition for antiperspirant benefit and comprising varying levels of oxybutynin.

The present invention involves the use of oligonucleotides known as siRNA in antiperspirancy and hyperhidrosis treatment.

siRNA are small interfering RNA molecules. Most of the siRNA are 20-25 nucleotides in length. siRNA are involved in RNA interference and regulate (interfere with; silence) gene expression, post-transcriptionally. The 20-25 nucleotide length seems to maximize target gene specificity over non-specific effects.

A large number of siRNA molecules for gene expression inhibition have been reported in EP1752536, EP2213738, WO2009/001359, and WO2010/080452 with possible use in pharmaceutical applications; however, none of these documents teaches or direct the use any of those oliogonucleotides for antiperspirancy.

Oligonucleotides have been disclosed for skin application in U.S. Pat. No. 7,087,743, U.S. Pat. No. 7,504,385, US2007/0134188, and WO2013/120726 where they are used for depigmentation of skin; however, none of these documents teaches or direct the use of oligonucleotides for antiperspirancy.

WO2014/107124 discloses a treatment of hyperhidrosis involving the reduction of ITRP2 protein function and the use specific siRNA molecules in such therapy.

It is thus an object of the present invention to provide a new and effective means for reducing perspiration and for the treatment of hyperhidrosis.

According to a first aspect of the invention, there is provided the use of an siRNA for reducing perspiration, wherein the siRNA is capable of at least one of: reducing levels of specified protein mRNA; reducing levels of specified protein; reducing specified protein calcium channel formation; reducing specified calcium channel function; wherein the specified protein is Orai1, Stim1, Orai3, TRPC1 or Stim2.

According to a second aspect of the invention, there is provided an siRNA for use in the treatment of hyperhidrosis, wherein the siRNA is capable of at least one of: reducing levels of specified protein mRNA; reducing levels of specified protein; reducing specified protein calcium channel formation; reducing specified protein calcium channel function; wherein the specified protein is Orai1, Stim1, Orai3, TRPC1 or Stim2.

According to a third aspect of the invention, there is provided an antiperspirant composition comprising a cosmetically acceptable carrier and an siRNA that is capable of at least one of: reducing levels of specified protein mRNA; reducing levels of specified protein; reducing specified protein calcium channel formation; reducing specified protein calcium channel function; wherein the specified protein is Orai1, Stim1, Orai3, TRPC1 or Stim2.

According to a fourth aspect of the present invention, there is provided a method of reducing perspiration comprising the topical application of a composition comprising a cosmetically acceptable carrier and an siRNA that is capable of at least one of: reducing levels of specified protein mRNA; reducing levels of specified protein; reducing specified protein calcium channel formation; reducing specified protein calcium channel function; wherein the specified protein is Orai1, Stim1, Orai3, TRPC1 or Stim2.

Herein, antiperspirant compositions and methods include compositions and methods suitable for the treatment of hyperhidrosis; indeed, the present invention is particularly suited to the treatment of hyperhidrosis.

Herein, preferred features of the invention apply equally to the use of an siRNA according to the first aspect of the invention; an siRNA for use in the treatment of hyperhidrosis according to the second aspect of the invention; antiperspirant compositions according to the third aspect of the invention andmethods of reducing perspiration according to the fourth aspect of the invention. Indeed, any feature of one aspect of the present invention may be used in any other aspect of the invention.

Herein, the word "comprising" is intended to mean "including" but not necessarily "consisting of" or "composed of." In other words, the listed steps or options need not be exhaustive.

Herein, all percentages are percentages by weight, unless otherwise indicated.

Herein, all numbers indicating amounts of material or conditions of reaction, physical properties of materials and/or use are to be understood as modified by the word "about", except in the examples, or where otherwise explicitly indicated.

Herein, numerical ranges expressed in the format "from x to y" include x and y. When for a specific feature multiple preferred ranges are described in the format "from x to y", it is understood that all ranges combining the different endpoints are also contemplated.

Antiperspirant compositions according to the invention are intended for topical application. Herein, topical application means application to the skin and does not mean application to the hair or internal cavities such as the mouth or nasal passages. Topical application to the underarm regions of the human body is particular effective. Preferably, application is directly onto the surface the human body.

Antiperspirant compositions according to the invention comprise a cosmetically acceptable carrier, but may take any physical form. Typical product formats include sprays, liquid roll-ons, gels, soft solids or sticks. Gels are a preferred product form.

During the course of their studies, the inventors have discovered specific calcium channel proteins and related proteins in the eccrine glands of humans. Further, they have found that such proteins and their function can be affected (reduced) by selected siRNA molecules, thereby reducing sweat secretion at its source.

Specific proteins identified as having relevance to human sweat production are Orai1, Stim1, Orai3, TRPC1 and Stim2.

The present invention utilizes an siRNA selected in accordance with specified functional and/or chemical parameters, selected after extensive research in this area.

The siRNA used in accordance with the present invention is capable of at least one of: reducing levels of specified protein mRNA; reducing levels of specified protein; reducing specified protein calcium channel formation; reducing specified protein calcium channel function; wherein the specified protein is Orai1, Stim1, Orai3, TRPC1 or Stim2.

Herein, reference to any of the specified proteins Orai1, Stim1, Orai3, TRPC1 or Stim2 should be understood to be with respect to their presence in human sweat glands, in particular human eccrine glands.

The present inventors have found that one or more of the functional parameters listed above: reducing levels of the specified proteins mRNA; reducing levels of the specified proteins; reducing the specified protein calcium channel formation and reducing the specified protein calcium channel function can lead to a reduction in perspiration.

Without wishing to be bound by theory, the siRNA used in the present invention is thought to interfere with the mRNA of a specified protein and thereby reduce the level of said protein in cells to which the siRNA gains access. The specified proteins relevant to the present invention are involved in the regulation of calcium levels within human cells, in particular human eccrine cells. Some of the proteins (Orai1, Orai3 and TRPC1) are themselves calcium channels proteins, whilst others (Stim1 and Stim2) are calcium sensors or "activators", closely involved in the activation of calcium channels in the plasma membrane.

Calcium levels in the cells of human eccrine glands are critical to sweat generation, this having been established previously (note WO 02/011690 and references cited therein). The present inventors have found a new method for manipulating intracellular calcium levels in such cells and thereby reducing perspiration.

Preferably, the siRNA used in accordance with the present invention is capable of at least one of: reducing levels of specified protein mRNA; reducing levels of specified protein; reducing specified protein calcium channel formation; reducing specified protein calcium channel function; wherein the specified protein is Orai1, Stim1, Orai3, or Stim2.

More preferably, the siRNA used in accordance with the present invention is capable of at least one of: reducing levels of specified protein mRNA; reducing levels of specified protein; reducing specified protein calcium channel formation; reducing specified protein calcium channel function; wherein the specified protein is Orai1, Stim1 or Stim2.

Most preferably, the siRNA used in accordance with the present invention is capable of at least one of: reducing levels of specified protein mRNA; reducing levels of specified protein; reducing specified protein calcium channel formation; reducing specified protein calcium channel function; wherein the specified protein is Orai1 or Stim1.

In certain preferred embodiments, a combination of siRNAs may be employed, selected from the group consisting of:
(i) An siRNA capable reducing the level of Orai1 and an siRNA capable of reducing the level of Stim1;
(ii) An siRNA capable reducing the level of Orai1 and an siRNA capable of reducing the level of Stim2;
(iii) An siRNA capable reducing the level of Orai1 and an siRNA capable of reducing the level of Orai3; and
(iv) An siRNA capable reducing the level of Orai1 and an siRNA capable of reducing the level of TRPC1.

In certain particularly preferred embodiments, a combination of siRNAs may be employed, selected from the group consisting of:
(i) An siRNA capable reducing the level of Orai1 and an siRNA capable of reducing the level of Stim1; and
(ii) An siRNA capable reducing the level of Orai1 and an siRNA capable of reducing the level of Orai3.

Orai1 and its function has been found to be affected by siRNA comprising a sequence selected from the group consisting of:
SEQ ID: 1 CCUUGACCGAGUUGAGAUUG; and a portion comprising at least 19 nucleotides thereof, wherein the siRNA size is from 19 to 30 nucleotides. A preferred siRNA of this type comprises SEQ ID: 1. A particularly preferred siRNA of this type is of SEQ ID: 1.

Stim1 and its function has been found to be affected by siRNA comprising a sequence selected from the group consisting of:
SEQ ID: 2 UGGAGUAACGGUUCUGGAUA; and a portion comprising at least 19 nucleotides thereof, wherein the siRNA size is from 19 to 30 nucleotides. A preferred siRNA of this type comprises SEQ ID: 2. A particularly preferred siRNA of this type is of SEQ ID: 2.

Orai3 and its function has been found to be affected by siRNA comprising a sequence selected from the group consisting of:
SEQ ID: 3 GAUUCAGUUCCUCUAGUUCC; and a portion comprising at least 19 nucleotides thereof, wherein the siRNA size is from 19 to 30 nucleotides. A preferred siRNA of this type comprises SEQ ID: 3. A particularly preferred siRNA of this type is of SEQ ID: 3.

TRPC1 and its function has been found to be affected by siRNA comprising a sequence selected from the group consisting of:
SEQ ID: 4 UGUUGUGAGCAACCACUUUG; and a portion comprising at least 19 nucleotides thereof, wherein the siRNA size is from 19 to 30 nucleotides. A preferred siRNA of this type comprises SEQ ID: 4. A particularly preferred siRNA of this type is of SEQ ID: 4.

Stim2 and its function has been found to be affected by siRNA comprising a sequence selected from the group consisting of:
SEQ ID: 5 UAUUGUAGUAUUGCACUUCU; and a portion comprising at least 19 nucleotides thereof, wherein the siRNA size is from 19 to 30 nucleotides. A preferred siRNA of this type comprises SEQ ID: 5. A particularly preferred siRNA of this type is of SEQ ID: 5.

In typical embodiments, the siRNA used in the present invention comprises a sequence selected from the group consisting of:
SEQ ID: 1 CCUUGACCGAGUUGAGAUUG;
SEQ ID: 2 UGGAGUAACGGUUCUGGAUA;
SEQ ID: 3 GAUUCAGUUCCUCUAGUUCC;
SEQ ID: 4 UGUUGUGAGCAACCACUUUG;
SEQ ID: 5 UAUUGUAGUAUUGCACUUCU; and
a portion comprising at least 19 nucleotides of any of the above nucleotide sequences, wherein the siRNA size is from 19 to 30 nucleotides.

In preferred embodiments, the siRNA used in the present invention comprises a sequence selected from the group consisting of:
SEQ ID: 1 CCUUGACCGAGUUGAGAUUG;
SEQ ID: 2 UGGAGUAACGGUUCUGGAUA;
SEQ ID: 3 GAUUCAGUUCCUCUAGUUCC;

SEQ ID: 5 UAUUGUAGUAUUGCACUUCU; and a portion comprising at least 19 nucleotides of any of the above nucleotide sequences, wherein the siRNA size is from 19 to 30 nucleotides.

In particularly preferred embodiments, the siRNA used in the present invention comprises a sequence selected from the group consisting of:
SEQ ID: 1 CCUUGACCGAGUUGAGAUUG;
SEQ ID: 2 UGGAGUAACGGUUCUGGAUA;

SEQ ID: 5 UAUUGUAGUAUUGCACUUCU; and a portion comprising at least 19 nucleotides of any of the above nucleotide sequences, wherein the siRNA size is from 19 to 30 nucleotides.

In especially preferred embodiments, the siRNA used in the present invention comprises a sequence selected from the group consisting of:
SEQ ID: 1 CCUUGACCGAGUUGAGAUUG;

SEQ ID: 2 UGGAGUAACGGUUCUGGAUA; and a portion comprising at least 19 nucleotides of any of the above nucleotide sequences, wherein the siRNA size is from 19 to 30 nucleotides.

The siRNA size is from 19 to 30 nucleotides. The siRNA that works to provide the benefits of the invention can be as small as 19 nucleotides long and in such cases the desired nucleotide may be any portion of the sequences claimed in the present invention. Alternately, the desired oligonucleotide may be as long as 30 nucleotides long and may comprise any one of the sequences in its entirety and in addition, a few nucleotides attached at one or both ends.

The siRNA is preferably present in a safe and effective amount in any composition of which it is a part. The siRNA is more preferably present in 0.00001 to 1%, more preferably 0.0001 to 0.01% by weight of the composition.

Compositions according to the invention comprise a cosmetically acceptable carrier. Such carrier is typically a fluid, the fluid comprising water in preferred embodiments, but being anhydrous in certain alternative embodiments of the invention.

Herein, an anhydrous carrier comprises less than 1')/0 of water and preferably less than 0.1%.

Herein, the term 'carrier' or 'cosmetically acceptable carrier' should be understood to include all components of the composition other than the siRNA, other antiperspirant active or deodorant active (excluding C1-C4 alcohols), and fragrance).

The cosmetically acceptable carrier may include components such as emollients and humectants. Such components are typically used at from 0.1 to 10%.

The cosmetically acceptable carrier may include oils, such as ester oils, ether oils, paraffin oils and silicone oils. Such components may be used at from 1 to 80%.

A preferred component in compositions of the invention is a fragrance, typically at a level of from 0.1 to 5% of the total composition. In compositions also comprising water, the fragrance is preferably accompanied by a fragrance solubiliser, typically a non-ionic surfactant used a concentration of from 0.1 to 5% of the total composition.

A further optional component is an organic anti-microbial agent. Such agents may be selected from any of those known in the art, provided reasonable skill is used to avoid any incompatibilities. An organic anti-microbial agent is a particularly preferred additional component when the composition used does not include a conventional, astringent aluminium containing antiperspirant salt. When employed, organic anti-microbial agents are typically used at a level of from 0.1 to 5% by weight of the composition.

Thickening agents may be employed in compositions of the invention. Such agents increase the viscosity of or solidify the carrier fluid in which the antiperspirant agent is typically suspended or dissolved.

Thickening agents may be selected from any of those known in the art, provided reasonable skill is used to avoid any incompatibilities. A preferred class of thickeners, especially for compositions also comprising water, are hydroxyalkyl celluloses, such as hydroxypropyl cellulose. When employed, thickening agents are typically used at a level of from 0.1 to 40%. When a hydroxyalkyl cellulose thickening agent is employed, this is typically used at a level of from 0.2 to 10% by weight.

A preferred component of the carrier of compositions according to the invention is a skin penetration enhancer (SPE). Such materials are capable of aiding the transport of the siRNA from the skin surface to the eccrine and/or apocrine secretory coil cells. It is highly preferably that such materials are co-soluble with the siRNA employed. The SPE can be a solvent for the siRNA, the siRNA preferably having a solubility in the SPE of greater than 50 $mmol \cdot dm^{-3}$, more preferably greater than 100 $mmol \cdot dm^{-3}$. Suitable SPEs include oleic acid, azone, urea, transcutol, and ethanol. Preferred SPEs are short chain polyhydric alcohols, in particular C2 to C5 alcohols with 2-5 hydroxy groups, especially glycerol and propylene glycol. The SPE may be present at a level of 0.5-90% by weight of the composition in which it is employed, excluding any propellant that may be present. Preferably, this level is 1-50% by weight, more preferably from 2-30%, and most preferably from 3-12%.

Particularly preferred SPEs are SPACE peptides and SPACE-lipid carrier systems as disclosed in *J. Controlled Release,* 173, 2014, 67-74 and *J. Controlled Release,* 179, 2014, 33-41. Such SPEs are preferably part of an ethosomal carrier system and may preferably include 1,2-dioleoyl-3-trimethylammonium-propane (DOPAC) as a building block or be conjugated to a phospholipid.

Compositions of the invention may comprise a combination of siRNAs as described earlier herein.

In some preferred embodiments, compositions according to the invention comprise an astringent antiperspirant salt, such as aluminum and/or aluminum-zirconium salt. When employed, such materials are typically present at from 1 to 50% of the composition of which they are part.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, exfoliating agents, pH adjusters, preservatives, natural extracts, essential oils, skin sensates, skin soothing agents, and skin healing agents.

The composition of the invention is targeted for cosmetic and dermal applications and is therefore preferably not for therapeutic/medical use, although such use is an alternative, non-excluded option.

In the following section, the invention is described by way of non-limiting examples.

EXAMPLES

Viable human eccrine sweat glands were isolated from samples of human skin (obtained under ethical consent) using the shearing method of Lee et al (1984).

Pre-designed siRNA duplexes for STIM1 and 2, Orai1, 3 and TRPC1 were purchased from Life Technologies, and transfection conditions were optimized using a TYE 563TM-labelled transfection control RNA duplex. A scrambled universal negative control duplex was used in all experiments. Isolated human eccrine gland secretory coil cells were transfected with 0.1 nM siRNA using Lipofectamine 2000 according to the manufacturer's instructions (Life Technologies). Transfected cells were subsequently harvested after 24 h for protein or mRNA assessment, or evaluated for store-operated $Ca^{2+}$ entry (SOCE, see below).

Intracellular $[Ca^{2+}]_i$ was measured in isolated eccrine glands by plating them onto Matrigel coated glass coverslips and loading them with the calcium-sensitive, fluorescent dye Fura-2 by incubation (30-45 min, 37° C.) with the membrane-permeant, acetoxymethyl ester form of the dye (Fura-2AM). These coverslips (with dye-loaded glands) were then mounted in a small chamber attached to the stage of an inverted microscope, and the glands superfused (ca. 5 ml $min^{-1}$, 37° C.) with physiological salt solution (PSS; composition (mM): NaCl 130, KCl 5, MgCl 1, CaCl 1, HEPES 20, D-Glucose 10, pH 7.4 with NaOH). Changes in $[Ca^{2+}]_i$ were detected using 340/380 nm excitation and 510 nm emission wavelengths, and data expressed as the 340:380 ratio. Further details on this technique may be found in the article by Roger Tsein et al in *J. Biol. Chem.*, 1985, 260, 3440-3450.

To measure store-operated calcium entry (SOCE), independent of external membrane receptor activation, the following assay protocol was used. First, isolated glands were exposed to 1 μM thapsigargin in $Ca^{2+}$-free PSS for 3 min. As thapsigargin inhibits the $Ca^{2+}$-ATPase uptake pathway in intracellular $Ca^{2+}$ stores, this enables $Ca^{2+}$ to leak out of the store and subsequently trigger the activation of SOCE. In $Ca^{2+}$-free PSS, this process is represented by a very small rise in $[Ca^{2+}]_i$. Glands were then exposed to 1 μM thapsigargin in $Ca^{2+}$-containing PSS for 2 min, thereby inducing a rapid increase in $[Ca^{2+}]_i$ via $Ca^{2+}$ entry into the cells via the open SOCE pathway. To complete the protocol, thapsigargin is finally removed by washing the glands with $Ca^{2+}$-containing PSS, and allowing the resting $[Ca^{2+}]_i$ level to re-establish itself, and the intracellular $Ca^{2+}$ stores to refill (see FIG. 1, further details below). In this study, the effectiveness of selected SOCE channel siRNA knock-downs were assessed by stimulating cells which had undergone knock-down with 1 μM thapsigargin, and comparing the magnitude of the response to that observed in control cells in which the wild-type SOCE channels were still expressed. Knock-down efficacy expressed as mean Fura-2 340/380 fluorescence ratios +/−S.E.M. (n=3, other than control: n=12) is shown in Table 1 and as % peak $[Ca^{2+}]_i$ relative to the 1 μM thapsigargin control (100%) in FIG. 2 (further details below).

FIG. 1 illustrates assay manipulations for assessing store-operated $Ca^{2+}$ entry (SOCE) by first triggering the release of intracellular $Ca^{2+}$ with 1 μM thapsigargin in a $Ca^{2+}$-free PSS, and then adding extracellular $Ca^{2+}$ to initiate $Ca^{2+}$ entry via activated SOCE channels.

Figure 2:
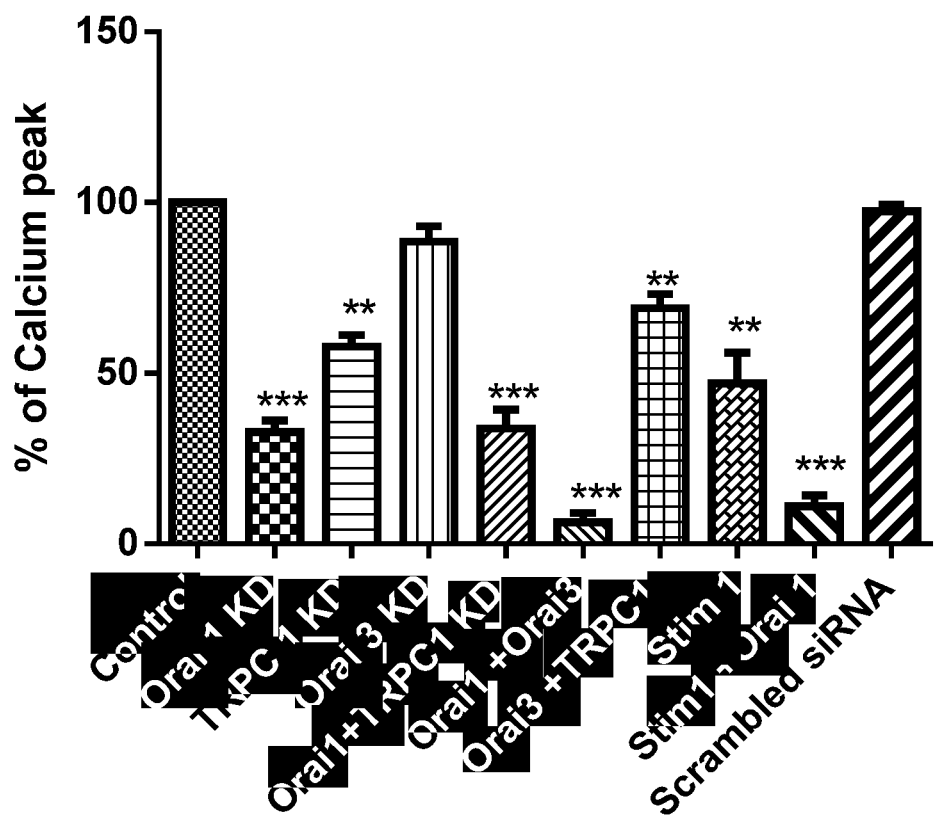

FIG. 2 is a representation of most of the data of Table 1 showing the effect of selected SOCE channel siRNA knock-downs on peak $[Ca^{2+}]_i$ activated by the application of 1 μM thapsigargin, as described above. 'Control' represents peak $[Ca^{2+}]_i$ induced by 1 μM thapsigargin (100%), and the effect of each SOCE knock-down is expressed as a % of the control.  represents P<0.001 and * represents P<0.0001.

TABLE 1

| siRNA(s) used (SEQ ID) | Protein(s) targeted | Mean 340/380 ratio | SEM |
| --- | --- | --- | --- |
| None | None | 0.403 | 0.002 |
| 1 | Orai1 | 0.131 | 0.012 |
| 3 | Orai3 | 0.356 | 0.025 |
| 4 | TRPC1 | 0.232 | 0.014 |
| 1 + 4 | Orai1 + TRPC1 | 0.136 | 0.031 |
| 1 + 3 | Orai1 + Orai3 | 0.025 | 0.092 |
| 3 + 4 | Orai3 + TRPC1 | 0.278 | 0.011 |
| 2 | Stim1 | 0.189 | 0.064 |
| 2 + 1 | Stim1 + Orai1 | 0.044 | 0.075 |
| 5 | Stim2 | 0.249 | 0.028 |
| 5 + 1 | Stim2 + Orai1 | 0.157 | 0.073 |
| Scrambled | None | 0.392 | 0.005 |

These results show the effect of selected SOCE channel siRNA knock-downs on the Fura-2 340/380 fluorescence ratio. The figures represent the recorded difference in 340/380 ratio between peak $[Ca^{2+}]_i$ (after the addition of extracellular $Ca^{2+}$) and resting $[Ca^{2+}]_i$ (in $Ca^{2+}$-free PSS) following the application of 1 μM thapsigargin (see FIG. 1). 'Control' represents the 340/380 ratio difference recorded following the application of 1 μM thapsigargin to untreated (wild type) eccrine gland secretory coil cells. SOCE was assessed using the protocol described in the text and illustrated in FIG. 1.

The results clearly illustrate effectiveness of the indicated siRNAs at reducing the calcium channel function. In vivo, this would result in reduced perspiration. It will be noted that knock-down of Orai1 using siRNA of SEQ ID. 1 is particularly effective and that the combined use of siRNA of SEQ ID 1 and SEQ ID 2 (knocking-down Orai1 and Stim1) is even more effective, as is the combined use of an siRNA affecting Orai1 and an siRNA affecting Orai3.

It will be noted that scrambled siRNA did not inhibit SOCE.

The invention claimed is:

1. A method of reducing perspiration comprising the topical application of a composition comprising a cosmetically acceptable carrier and an siRNA that is capable of at least one of: reducing levels of specified protein mRNA; reducing levels of specified protein; reducing specified protein calcium channel formation; reducing specified protein calcium channel function; wherein the specified protein is selected from the group consisting of Orai1, Stim1, Orai3, TRPC1 and Stim2, wherein the siRNA comprises a sequence selected from the group consisting of:
SEQ ID: 1 CCUUGACCGAGUUGAGAUUG;
SEQ ID: 2 UGGAGUAACGGUUCUGGAUA;
SEQ ID: 3 GAUUCAGUUCCUCUAGUUCC;
SEQ ID: 4 UGUUGUGAGCAACCACUUUG;
SEQ ID: 5 UAUUGUAGUAUUGCACUUCU; and
a portion comprising at least 19 nucleotides of any of the above nucleotide sequences, wherein the siRNA size is from 20 to 30 nucleotides.

2. The method of reducing perspiration according to claim 1, wherein the specified protein is selected from the group consisting of Orai1, Stim1, Stim2, and Orai3.

3. The method of reducing perspiration according to claim 2, wherein the siRNA comprises a sequence selected from the group consisting of:
SEQ ID: 1 CCUUGACCGAGUUGAGAUUG;
SEQ ID: 2 UGGAGUAACGGUUCUGGAUA;
SEQ ID: 3 GAUUCAGUUCCUCUAGUUCC;
SEQ ID: 5 UAUUGUAGUAUUGCACUUCU; and
a portion comprising at least 19 nucleotides of any of the above nucleotide sequences, wherein the siRNA size is from 20 to 30 nucleotides.

4. The method of reducing perspiration according to claim 1, wherein the specified protein is selected from the group consisting of Orai1, Stim1, and Stim2.

5. The method of reducing perspiration according to claim 4, wherein the siRNA comprises a sequence selected from the group consisting of:
SEQ ID: 1 CCUUGACCGAGUUGAGAUUG;
SEQ ID: 2 UGGAGUAACGGUUCUGGAUA;
SEQ ID: 5 UAUUGUAGUAUUGCACUUCU; and
a portion comprising at least 20 nucleotides of any of the above nucleotide sequences, wherein the siRNA size is from 19 to 30 nucleotides.

6. The method of reducing perspiration according to claim 2, wherein the specified protein is Orai1 or Stim1.

7. The method of reducing perspiration according to claim 6, wherein the siRNA is an oligonucleotide comprising a sequence selected from the group consisting of:
   SEQ ID: 1 CCUUGACCGAGUUGAGAUUG;
   SEQ ID: 2 UGGAGUAACGGUUCUGGAUA; and
   a portion comprising at least 19 nucleotides of any of the above nucleotide sequences, wherein the siRNA size is from 19 to 30 nucleotides.

* * * * *